United States Patent [19]

Eser et al.

[11] Patent Number: 5,759,488
[45] Date of Patent: Jun. 2, 1998

[54] METHOD AND APPARATUS FOR DISINFECTING OR STERILIZING INFECTIOUS WASTE

[76] Inventors: Hermann Eser, Regina-Ullmann-Strasse 73, D-81927 Munich; Eduard Kneifel, Bussardstrasse 26, D-82008 Unterhaching, both of Germany

[21] Appl. No.: 621,238

[22] Filed: Mar. 25, 1996

[30] Foreign Application Priority Data

Mar. 31, 1995 [EP] European Pat. Off. ............ 95104819

[51] Int. Cl.[6] ...................................................... A61L 2/08
[52] U.S. Cl. ............................ 422/26; 422/33; 250/432 R
[58] Field of Search ............................ 422/26, 28, 33; 250/432 R

[56] References Cited

U.S. PATENT DOCUMENTS

| 4,325,417 | 4/1982 | Boggs et al. | 141/98 |
|---|---|---|---|
| 4,396,582 | 8/1983 | Kodera | 422/31 |
| 4,400,357 | 8/1983 | Hohmann | 422/299 |
| 5,039,495 | 8/1991 | Kutner et al. | 422/299 |
| 5,132,084 | 7/1992 | Harrell et al. | 422/295 |
| 5,362,443 | 11/1994 | Tanaka et al. | 422/295 |
| 5,413,757 | 5/1995 | Kutner et al. | 422/21 |
| 5,480,610 | 1/1996 | Birkholz et al. | 422/26 |
| 5,545,383 | 8/1996 | Zwingenberger et al. | 422/26 |

FOREIGN PATENT DOCUMENTS

| 4225430 | 2/1994 | Germany . |
|---|---|---|
| 4417512 | 11/1994 | Germany . |
| 94/00162 | 1/1994 | WIPO . |

*Primary Examiner*—Peter A. Hruskoci
*Assistant Examiner*—Betsey J. Morrison
*Attorney, Agent, or Firm*—MacMillan, Sobanski & Todd

[57] ABSTRACT

A method for disinfecting or sterilizing infectious waste is described in which infectious waste is introduced into a pressure chamber, the pressure chamber is evacuated, a fluid fed in so as to fill the pressure chamber with saturated steam, the infectious waste remains for a specified disinfection or sterilization period in the heated saturated steam and the pressure chamber is then aerated so as to remove the disinfected or sterilized waste. An apparatus for performing the method is also described, this apparatus comprising one or more pressure vessels (2) which each have at least one access means (3) and at least one infrared radiation source. The dimensions of these pressure vessels (2) are preferably not much greater than a plastic collecting container for the infectious waste.

7 Claims, 5 Drawing Sheets

METHOD AND APPARATUS FOR DISINFECTING OR STERILIZING INFECTIOUS WASTE

The invention is concerned with a method and an apparatus for disinfecting or sterilizing infectious waste. Such infectious waste, which first has to be disinfected or sterilized before it can be further treated, accrues for example in hospitals.

An apparatus for treating infectious waste by means of microwaves is known from DE-OS 37 10 156. This apparatus comprises a microwave chamber fitted with isolation doors on opposite sides. A conveyor belt which can be moved alternately backward and forward or a turntable is arranged between the two isolation doors, and inside the chamber are provided several microwave transmitters thereabove. The infectious waste to be treated and located inside a sealed container permeable to microwaves is placed on to the conveyor belt or turntable and then exposed to infrared radiation, while the container is moved alternately backward and forward or is alternately rotated around the turntable axis. The container's movement is intended to cause all the regions of the infectious waste to be exposed to microwaves. A fluid bag which bursts on exposure to microwaves can also be provided in the container so as to moisten the infectious waste.

This known apparatus and its associated treatment method encounter considerable problems in that it cannot necessarily be ensured that the infectious waste is actually disinfected or sterilized after it has been treated. This is because the microwaves alone do not have a disinfecting or sterilizing effect; rather the treatment only takes effect by the microwaves heating up a medium such as water and by the infectious waste being disinfected or sterilized by this heated medium. This known solution therefore entails the risk that the operating personnel forgets to introduce the fluid bag and that disinfection or sterilization does not take place when there is insufficiently moist infectious waste.

To solve this problem of the addition of liquid to the infectious-waste container being forgotten, EP 0 410 306 A2 suggests a method and an apparatus for sterilizing waste, particularly hospital waste, in which method plastic containers filled with infectious waste are pierced with injection needles in order to inject a disinfectant into the inside of the plastic containers.

For this purpose, an additional number of special plastic containers filled with infectious waste is placed on a preparation conveyor belt inside an isolation chamber. After the isolation chamber's entry door has been sealed, an isolation door leading to a sterilization chamber is opened and the plastic containers are passed from the preparation conveyor belt to a main conveyor belt within the sterilization chamber. After the sterilization chamber has been sealed, a plurality of mobile injection needles corresponding to the number of containers is punctured from above into corresponding incision points in the lids of the plastic containers. After water or disinfectant has been injected into the plastic containers, the containers in the sterilization chamber are exposed to microwaves in order to perform sterilization. The injection needles are then withdrawn again and after a door has been opened, the containers can be removed at the discharge end of the main conveyor belt. EP 0 410 306 A2 also suggests that a further second injection needle be respectively punctured into the containers so as to remove excess gases, thus avoiding an overpressure in the plastic container.

Although the proposed method solves the problem that the introduction of liquid into the plastic container filled with infectious waste is inadvertently forgotten, the known solution is extremely complex in terms of the incision mechanism for the injection needles and in terms of the necessary precise positioning of the containers in relation to the injection needles so as to ensure that the injection needles accurately enter the incision points provided in the container lids. Finally there is the problem that the plastic containers virtually do not withstand any significant pressure load, with the result that the pressures arising during treatment inside the plastic container cannot be set such as would be ideal for disinfection or sterilization of infectious waste.

The German Health Bulletin 30, No. 8, August 1987, describes a fractional vacuum method in which the disinfection of objects is performed inside a vacuum-tight disinfection chamber. The air is removed from the chamber and from the disinfection material as a result of multiple evacuation in exchange for saturated steam being allowed to flow in; disinfection then takes place by means of saturated steam and the disinfection material is finally dried by evacuation of the chamber. In practice, such methods are performed at very high pressures and temperatures, thereby requiring complex and expensive installations. The saturated steam is generated externally and then supplied to the evacuated chamber. Although this previously known method produces extremely good sterilization results, it does however entail cost-intensive, stationary installations.

The invention is based on the problem of creating a method and an apparatus for disinfecting or sterilizing infectious waste by means of which a reliable disinfection or sterilization of the infectious waste can be achieved cost-effectively.

In the method according to the invention, the infectious waste to be treated is first placed inside a pressure chamber. The pressure chamber is then evacuated in order to produce, as a result of removing air and gases from the chamber and from the infectious waste, optimum conditions for creating an atmosphere composed of saturated steam. A fluid is then fed into the pressure chamber. This fluid may be a liquid which evaporates on account of the vacuum inside the pressure vessel or it may be pre-evaporated saturated steam. The amount of fluid is selected such that at least the pressure chamber's volume is completely filled with saturated steam. The infectious waste to be treated then remains in the heated saturated steam inside the pressure chamber for a predetermined dwell period needed for disinfection or sterilization. The pressure chamber is finally aerated and the disinfected or sterilized waste can be removed.

A reliable disinfection or sterilization of the infectious waste is ensured in the method according to the invention, because evacuation of the pressure chamber guarantees that after the liquid has been fed into the pressure chamber, only saturated steam, without any interfering gases, is in fact present, which in conjunction with a corresponding temperature of the saturated steam is a prerequisite for proper disinfection or sterilization. Since the steam is heated to the temperature required for disinfection or sterilization before the fluid enters the pressure chamber, the method according to the invention can be implemented cost-effectively.

Although a method, which operates with a vacuum and steam for disinfecting and sterilizing infectious waste, is already known from the previous German Patent P 44 07 311, which in turn does not yet constitute a prior publication, microwave radiation is used in this method for the purpose of heating up the fluid and for melting open a reference rupture point. Since particular screening measures need to be taken in methods which operate using microwave radiation, such methods entail relatively complex apparatus.

In the method according to the invention, water can be used as a fluid which is fed into the pressure chamber. Since no disinfectants are therefore needed, there is a cost saving.

According to the invention, it is favorable to perform several cycles after saturated steam has been fed into the pressure chamber and then to re-evacuate the pressure chamber in order to minimize the saturated steam's residual air content and the condensation inside the pressure chamber. The walls of the pressure vessels are likewise heated so as to prevent formation of condensate too.

A preferred embodiment of the invention's method relates to the treatment of infectious waste present in sealed containers made for example of plastic. This is because infectious waste, as accrues in hospitals for example, is usually first collected in a container and then, in this sealed container, is taken to be treated by disinfection or sterilization. The container should not however be opened any more before treatment so that no contamination of the environment is caused by escaping germs or bacteria. This problem that on the one hand, the infectious waste is to be disinfected in the container by hot saturated steam, while the container, on the other hand, is not to be opened any more outside of the treatment chamber, is solved according to the invention in that once the container with its infectious waste is introduced into the pressure chamber during subsequent evacuation of the pressure chamber, infrared radiation is simultaneously introduced into the pressure chamber in order to open a reference rupture point provided in a container wall and which can be melted open by infrared radiation, thereby creating a gas-permeable connection between the container's interior and the pressure chamber. The difference in pressure between the container's interior and the pressure chamber during the pressure chamber's evacuation additionally helps to melt out the reference rupture point in the container. The reference rupture point, which infrared radiation causes to melt open, is therefore also pressed out of the container by the overpressure arising during evacuation and found inside the container compared to the pressure chamber. The infrared radiation merely needs to be applied during a period necessary to melt open the reference rupture point reliably. After an opening in the container has been automatically produced in this manner and if there is further evacuation of the pressure chamber, the inside of the container with the infectious waste is then simultaneously evacuated as well. In consequence, the heated saturated steam can penetrate through the opened reference rupture point into the container's interior and can cause the infectious waste to be disinfected.

In this embodiment of the method according to the invention, the infectious waste to be treated in a closed container fitted with a reference rupture point which can be melted open by infrared radiation, such as a plastic container sealed with a lid or a sealed plastic bag, can therefore be introduced into the treatment chamber without having to open the container beforehand. Whereas the initially described, previously known solutions entail the risk either that the operating personnel forget to insert a fluid bag into the collecting container for the infectious waste or that a very intricate mechanism with mobile injection needles is needed for automatically supplying fluid to the container's interior, the problem of reliably exposing the infectious waste to a heated atmosphere of saturated steam is solved according to the invention in a simple manner without manual or mechanical intervention being necessary.

The fact that after melting above the reference rupture point, the inside of the container with the infectious waste is also evacuated, reliably ensures that the infectious waste is in fact exposed to a pure atmosphere of saturated steam. In the initially described methods, however, the collecting container with the infectious waste is always filled with air; furthermore, other gases may have been formed therein, since no influence can be exerted on what has been individually collected in the container. Yet an evacuation of the collecting container's interior is not possible in the previously known methods, as the plastic containers used would not withstand the resultant underpressure. The known methods are therefore likewise unable to create an atmosphere of saturated steam with an overpressure in the collecting containers for infectious waste, since the container would otherwise burst. In contrast, according to the invention, an overpressure of the saturated-steam atmosphere merely has an effect on the purpose-built pressure chamber and not on the container in which the infectious waste is introduced into the pressure chamber, because a pressure compensation is achieved by the gas-permeable connection between the inside of the container and the pressure chamber.

So as to disinfect infectious waste using the method according to the invention, it is expedient to heat the saturated steam up to a temperature of $\geq 105°$ C. A suitable higher temperature level than for disinfection is then necessary for sterilization.

A particularly economical embodiment of the invention's method is represented by the ability to operate the installation in a push-pull or alternating mode if there are at least two pressure vessels. One of the pressure vessels is evacuated while the other is dampened.

An apparatus according to the invention for performing the above described method comprises a pressure vessel fitted with at least one access means for introducing and removing the infectious waste and with at least one infrared radiation source; this apparatus also comprises a supply system for evacuating/aerating the pressure vessel and for feeding fluid into the pressure vessel, as well as a control, regulating and monitoring system.

Since in the method according to the invention, the whole of the pressure vessel's interior is disinfected or sterilized in each treatment cycle, the invention's apparatus can dispense with complex isolation systems and upstream isolation chambers.

The apparatus for performing the method according to the invention can therefore be constructed compactly and with relatively little design input, which in turn results in a cost-effective solution.

Since neither an isolation system and nor conveyance means are required inside the pressure chamber in order to move containers filled with infectious waste backward and forward or to position them, as is the case of conventional apparatus, several pressure vessels can be advantageously integrated within one apparatus on account of the pressure vessels' compact design as enabled by the invention. Each pressure vessel is fitted with its own access means and its own source of infrared radiation. In an advantageous manner, these pressure vessels have a joint supply system and a joint control, regulating and monitoring system. An installation is therefore created which can be adapted with considerable flexibility to the respective requirements of the infectious waste to be treated, thereby reducing the energy and costs expended on the treatment of the infectious waste.

So as to obtain a compact and cost-effective apparatus, it is advantageous for the pressure vessel to have internal dimensions which are greater than predetermined maximum dimensions for an infectious-waste collecting container only by as much as is necessary to enable such a collecting container with these maximum dimensions to be comfortably accommodated in the pressure vessel. Such a pressure vessel is therefore not much larger than a predetermined collecting container for infectious waste. An individual collecting container with infectious waste can thereby also be treated with minimum expenditure of time and energy, and a considerably larger volume than corresponds to the volume of the collecting container with infectious waste does not need to be evacuated, filled with saturated steam or heated up.

Due to the compact dimensions of an individual pressure vessel, several pressure vessels can, as already previously mentioned, be combined in a modular manner to form an installation in which a number, corresponding to the specific requirement, of collecting containers for infectious waste can be simultaneously treated. The dimensions of the various pressure vessels of an installation can of course vary in size, but it is expedient to provide identical pressure vessels of a certain standard size in order to keep the installation's production costs to a minimum.

Preferably, just one access means is provided per pressure vessel. It is particularly advantageous for the pressure vessel to be designed such that part of the pressure vessel can be opened. The infectious waste can in this manner be comfortably introduced into the pressure vessel. After the mobile part of the pressure vessel has been opened, the collecting containers for infectious waste can, in a sealed state, be placed or laid directly inside the pressure vessel, and after the foldable part of the pressure vessel has been sealed, the treatment cycle can be started immediately for the disinfection or sterilization of the infectious waste. The treated infectious waste is then removed in the same manner in that the container with the waste is directly removed from the pressure vessel once more. A rapid, direct loading and unloading of the pressure vessels is therefore possible. Thanks to the time that can be saved, there is a drop in operating costs compared to conventional installations in which time-consuming isolation systems have to an extent to be negotiated when loading and unloading.

Just one infrared radiation source per pressure vessel is provided respectively in a preferred embodiment. This infrared radiation source can then be adapted to an optimum extent to the requirements in terms of radiation energy needed for a pressure vessel. The design input for the apparatus according to the invention can therefore be reduced and the apparatus consequently produced cost-effectively and distributed economically. If several pressure vessels are combined to form an installation, just those pressure vessels which are actually filled with infectious waste are respectively systematically exposed to infrared radiation by the infrared radiation sources individually provided at the pressure vessels. The invention's installation comprising several pressure vessels can therefore be adapted in an optimum manner to the volume of infectious waste to be treated, and no more pressure vessels than necessary are exposed to infrared radiation and filled with heated saturated steam. The invention's apparatus therefore operates in a very energy-saving and cost-effective manner and is extremely flexible in terms of the quantity of infectious waste to be treated.

The apparatus according to the invention is preferably mounted to a chassis and operated in a mobile fashion, but it can also of course be operated in a stationary manner. It is expedient, as previously described, to combine several pressure vessels and to provide them with a joint supply system and a joint control, regulating and monitoring system.

According to the invention, the form of an individual pressure vessel can be selected such as is most advantageous for the particular application. From the point of view of a compact combination of several pressure vessels to form an installation, a decisive factor is for example the criterion that the individual pressure vessels can be arranged side by side with as little loss of space as possible and that the available volume of pressure vessels is utilized as well as possible. In this regard, substantially cuboid pressure vessels may for example be advantageous. The pressure vessels can however also have a barrel-shaped design, for instance with a circular cross section. The shape of the pressure vessels does of course also depend on the shape of the collecting containers for the infectious waste, which are to be accommodated by the pressure vessel for the treatment of infectious waste, and vice versa.

The infrared radiation sources can be arranged on the pressure vessels at any position suitable for melting open the reference rupture point, e.g. at the top of the pressure vessel, to the side or below the pressure vessel. The irradiation into the vessel can take place through a window permeable to the infrared radiation used.

A particularly advantageous embodiment of the apparatus is that containers for infectious waste, the plastic lids of which are fitted with a layer that absorbs infrared radiation, are used. The coating which absorbs infrared radiation causes the plastic lid in this area be to heated up to a particularly considerable extent during infrared irradiation, which ultimately causes the plastic lid to melt open. The pressure gradient prevalent in the pressure chamber assists and accelerates the opening process.

A useful embodiment of the apparatus according to the invention is represented by the use of a reflector which focuses the infrared radiation in such a way that the focal point is below the plastic container's surface which still has to be melted. This enables containers of varying heights to be melted open, since the focal point is below the surface of the lowest container.

According to the invention, the installation can be set up in a modular fashion in groups of two, thereby avoiding unnecessarily large volumes and saving on time and energy. For instance, just one group or pressure vessel can be operated at minimum utilization.

BRIEF DESCRIPTION OF THE DRAWINGS

An exemplary embodiment of an apparatus functioning according to the invention's method will now be described in greater detail with reference to the attached drawings.

Figure 1:
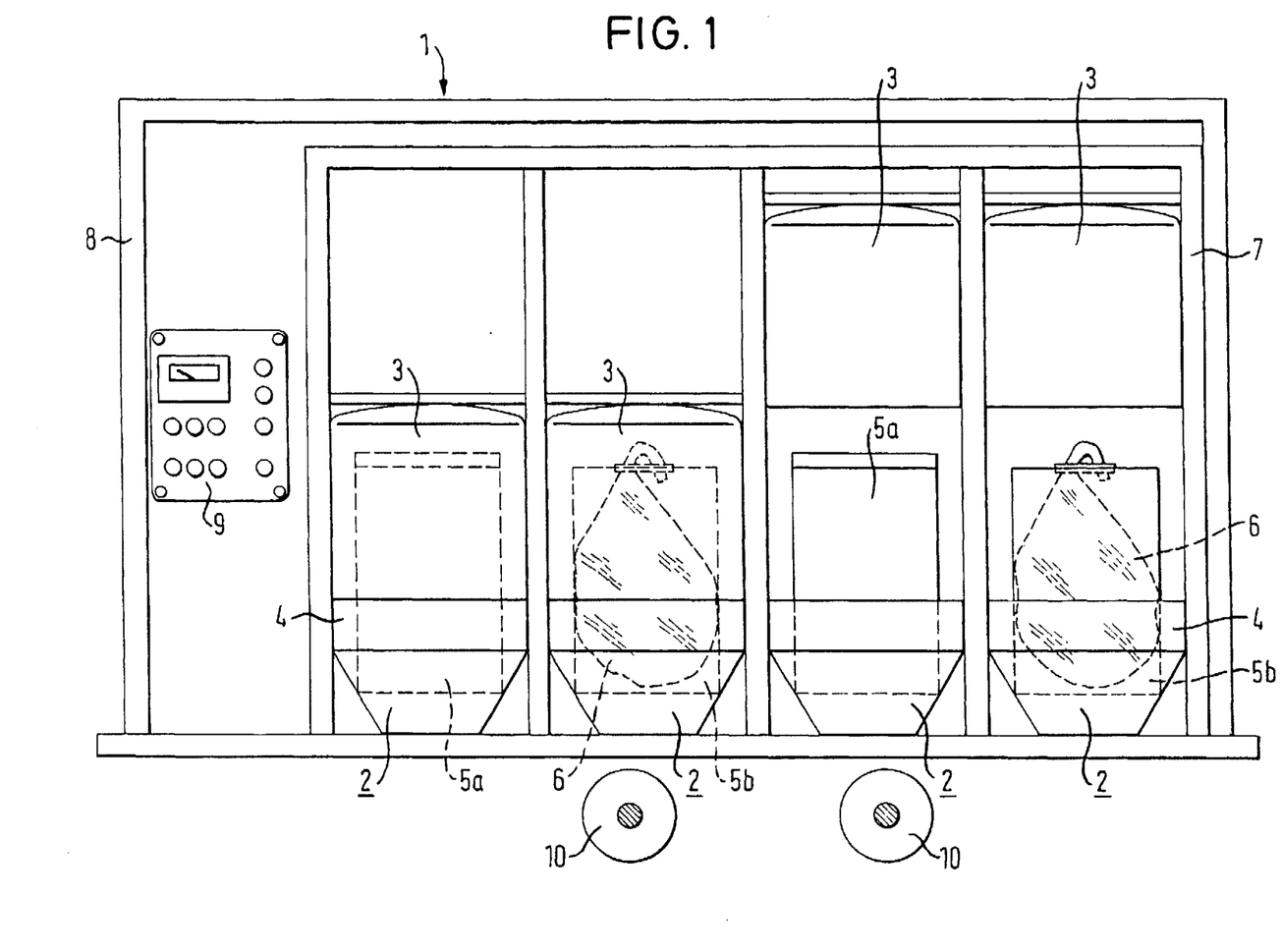
FIG. 1 shows a side view of a disinfection installation according to the invention.

FIG. 1 shows an installation 1 for disinfecting infectious waste and comprising four identically designed pressure vessels 2. The four pressure vessels 2 are arranged side by side inside a frame 7 which in turn is held by a container 8. The entire system inside container 8 is mounted on to a chassis 10 which is only schematically represented. The installation can for example be mounted as an assembly on a truck or on a trailer so that it can be operated in a mobile fashion.

Pressure vessels 2 each comprise an upper part 3 which can be opened and a rigidly mounted lower part 4. Both the left-hand pressure vessels 2 are shown in a sealed state in FIG. 1, while both the right-hand pressure vessels 2 are shown in an opened state. In the drawing, two of the pressure vessels 2 are filled with plastic containers 5a which are each sealed with a lid and in which the infectious waste to be treated is located. The other two pressure vessels 2 are each filled with an open plastic container 5b and a plastic waste bag 6 contained therein. The infectious waste is located inside the sealed plastic waste bag. The four pressure vessels 2 can therefore be individually loaded with infectious waste by opening fold-up upper parts 3. A control panel 9 for controlling the disinfection treatment in the pressure vessels is provided in container 8 in addition to the four pressure vessels 2.

Figure 2:
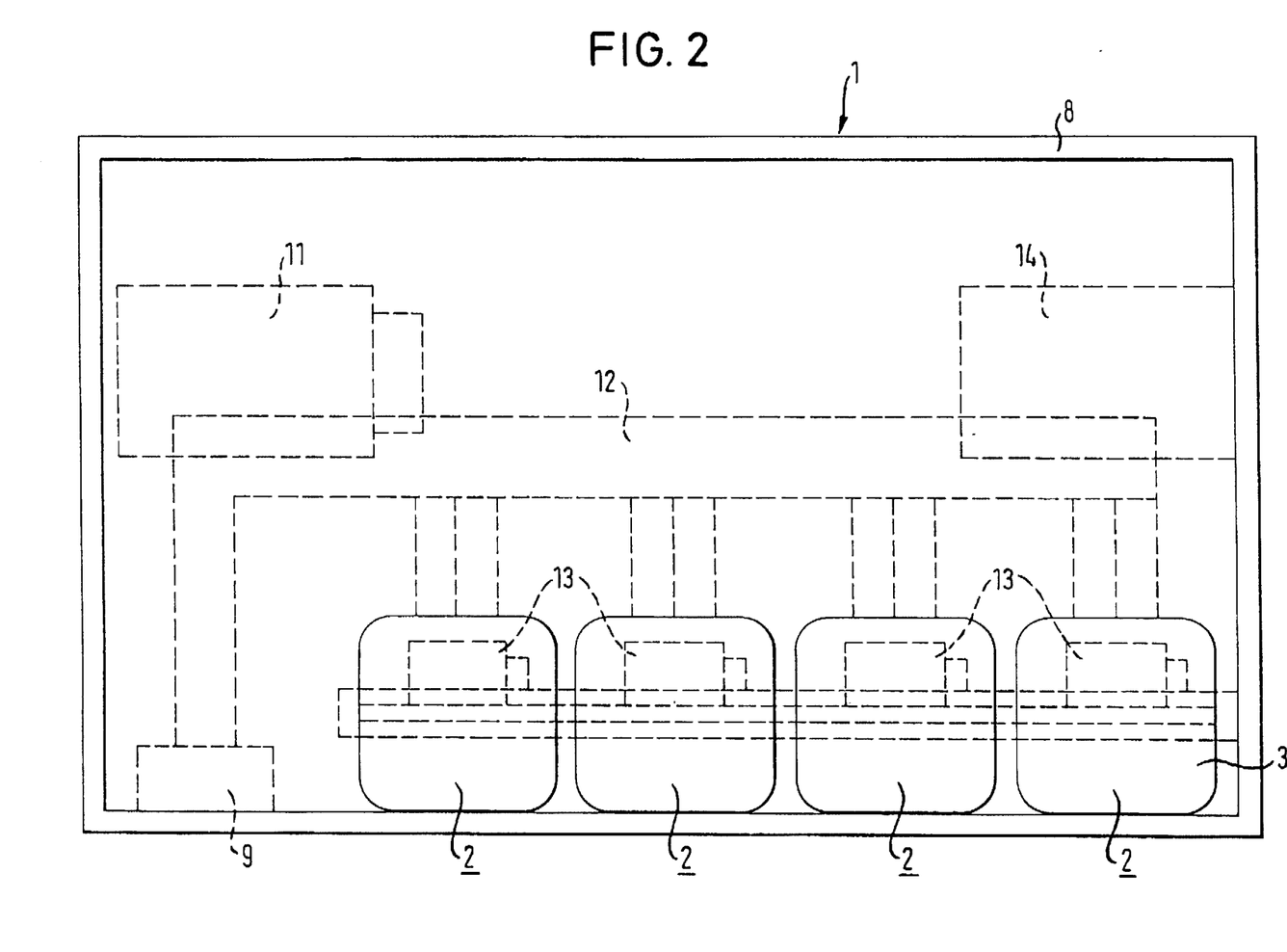
FIG. 2 shows a horizontal projection of the installation in FIG. 1.

The arrangement of the four pressure vessels 2 in container 8 is evident in FIG. 2. Each pressure vessel 2 has an opening mechanism 13 with which the pressure vessel's mobile upper part 3 can be opened and pressure-sealed again.

The four pressure vessels 2 are combined into an assembly group and have joint control and operating means. Control and supply lines 12 are schematically represented in FIG. 2. A vacuum pump 11 and a water tank 14 of the installation are also shown in container 8.

Figure 3:
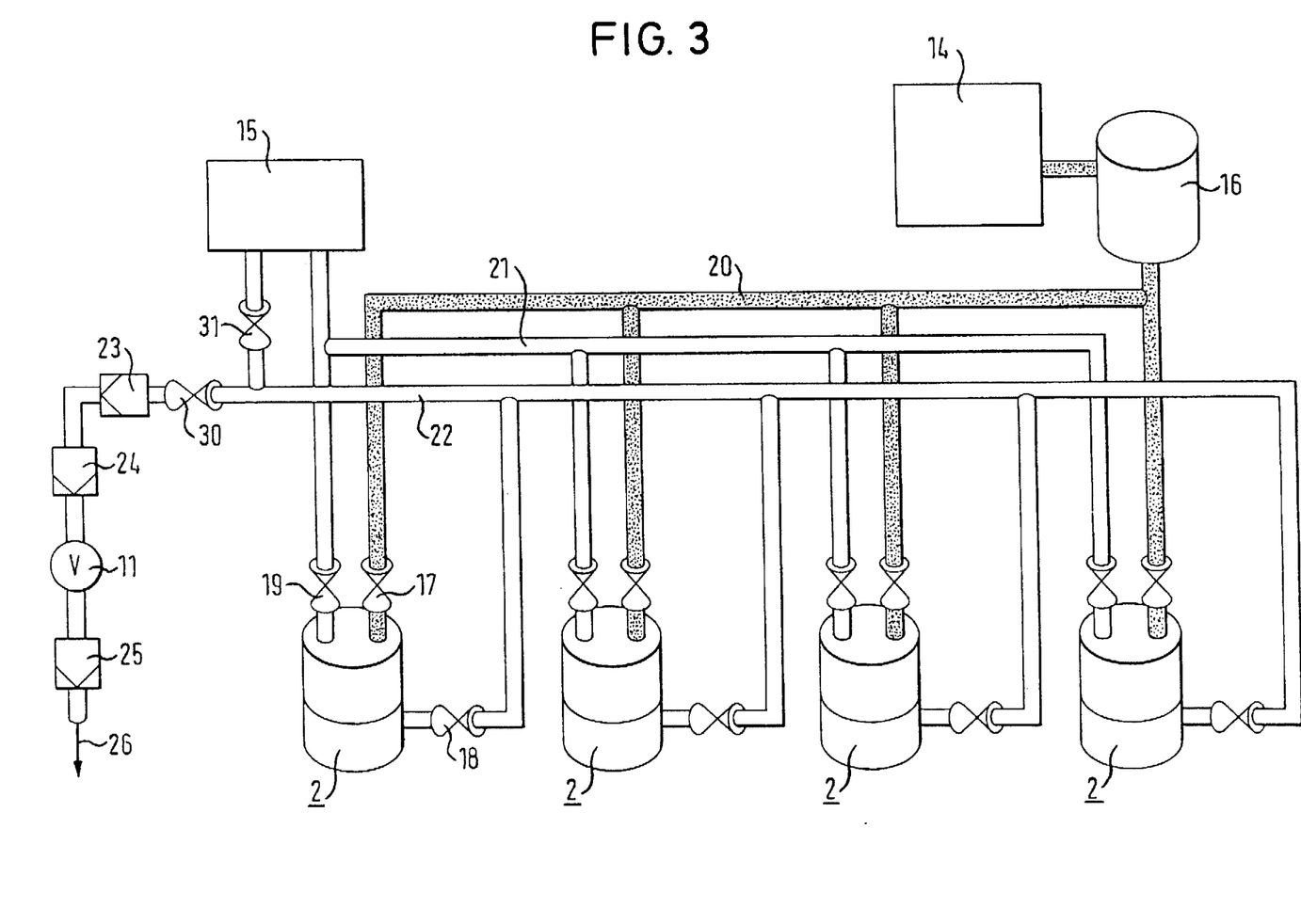
FIG. 3 shows a schematic diagram of the layout of the installation in FIG. 1.

The layout of the supply and operating systems of the installation represented in FIGS. 1 and 2 is shown schematically in FIG. 3.

The four pressure vessels 2 are each connected via an air shutoff valve 18 to a joint airing and ventilation line 22. Airing and ventilation line 22 is connected via a shutoff valve 30 to a bacterial filter 23 which has a water trap. Downstream of the first bacterial filter 23 and water trap is a second bacterial filter 24 to which vacuum pump 11 is connected. Downstream of vacuum pump 11 is a charcoal filter 25 which issues into an air outlet 26.

Each pressure vessel 2 is respectively connected via a water inlet valve 17 to a water line 20 which is fed by a water tank 14. A boiler or flow heater 16 is provided in water line 20 so as to heat up the feed water from water tank 14 before it is fed to the individual pressure vessels 2.

Each pressure vessel 2 is finally fitted with a relief valve 19 to which an overpressure line 21 is connected which is in turn connected to an overpressure vessel 15. Overpressure vessel 15 is in turn connected via a shutoff valve 31 to aerating and ventilating line 22.

Figure 4:
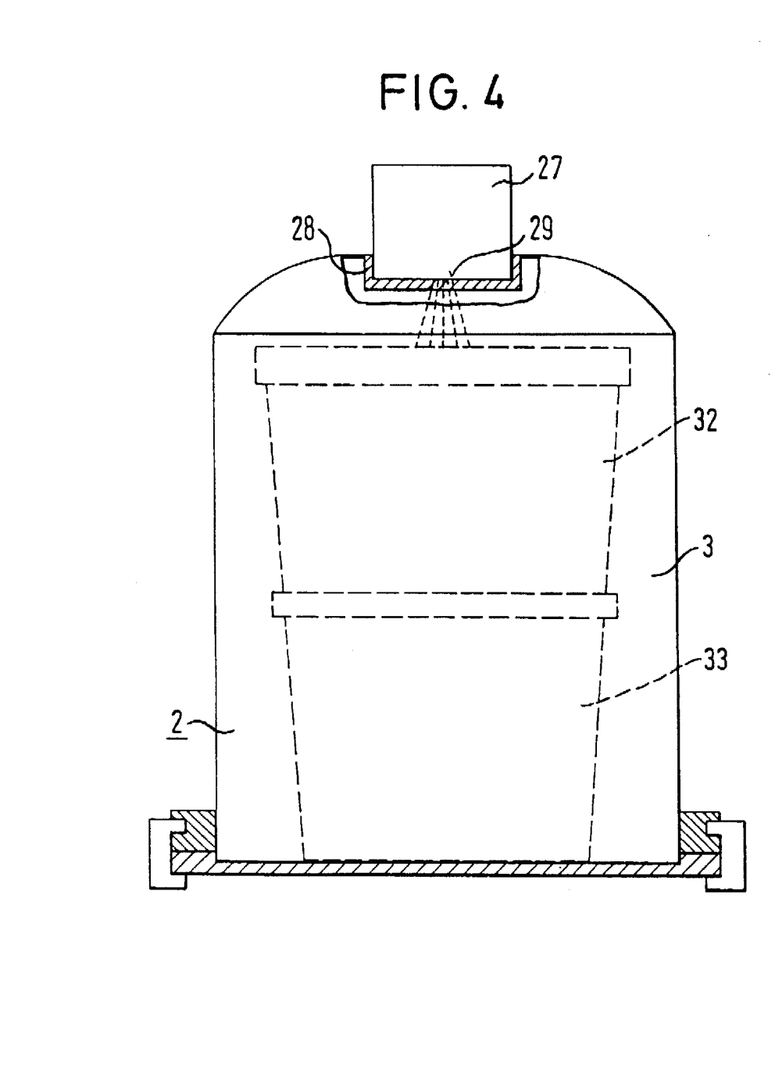
FIG. 4 shows a longitudinal section of an upper pressure-vessel part with an infrared radiation source according to the invention.
Figure 5:
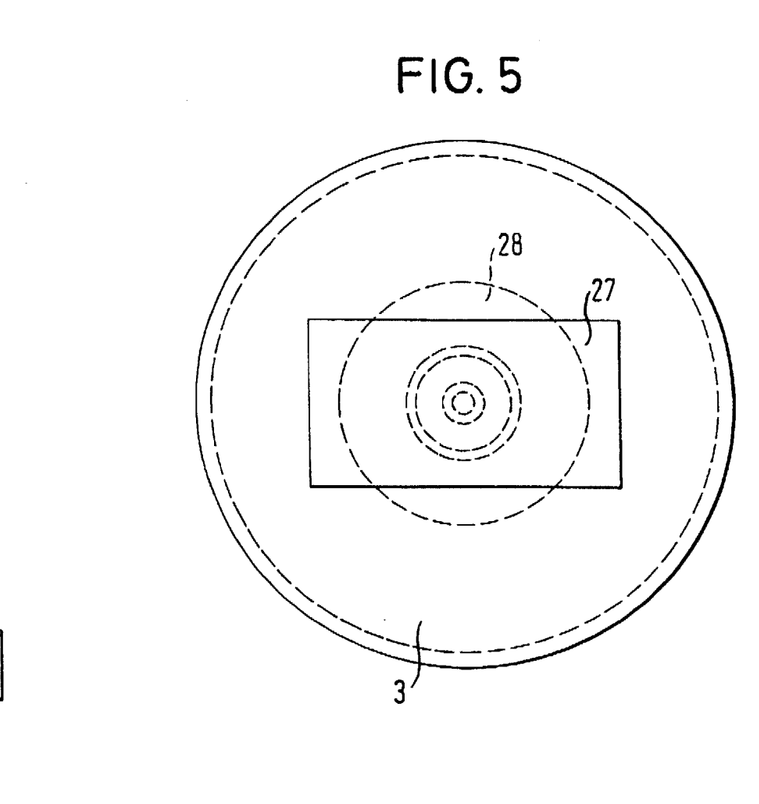
FIG. 5 shows a horizontal projection of the upper pressure-vessel part with infrared radiation source in FIG. 4.

Each pressure vessel 2 is fitted with an infrared radiation source which is not however shown in FIGS. 1 to 3. Such an infrared radiation source 27, as arranged in each pressure vessel 2, is shown in FIG. 4. In the exemplary embodiment, an infrared radiation source 27 is arranged externally on the upper side of lift-up upper part 3 of pressure vessel 2. This radiation source can however also be located at another suitable site. An opening 29 through which the infrared radiation source is irradiated into the interior of pressure vessel 2 is provided in upper part 3. Opening 29 and a part of the infrared radiation source 27 protruding into the inside of pressure vessel 2 is provided with an infrared-permeable cover 28 in the interior of the pressure vessel. This cover 28 is used to protect the infrared radiation source from pressure, moisture and heat which arise inside the pressure vessel. FIG. 5 shows the arrangement of infrared radiation source 27 and cover 28 centrally at the upper side of the pressure vessel's lift-up upper part 3. Two infectious-waste containers 32, 33 of varying size are indicated.

Figure 6:
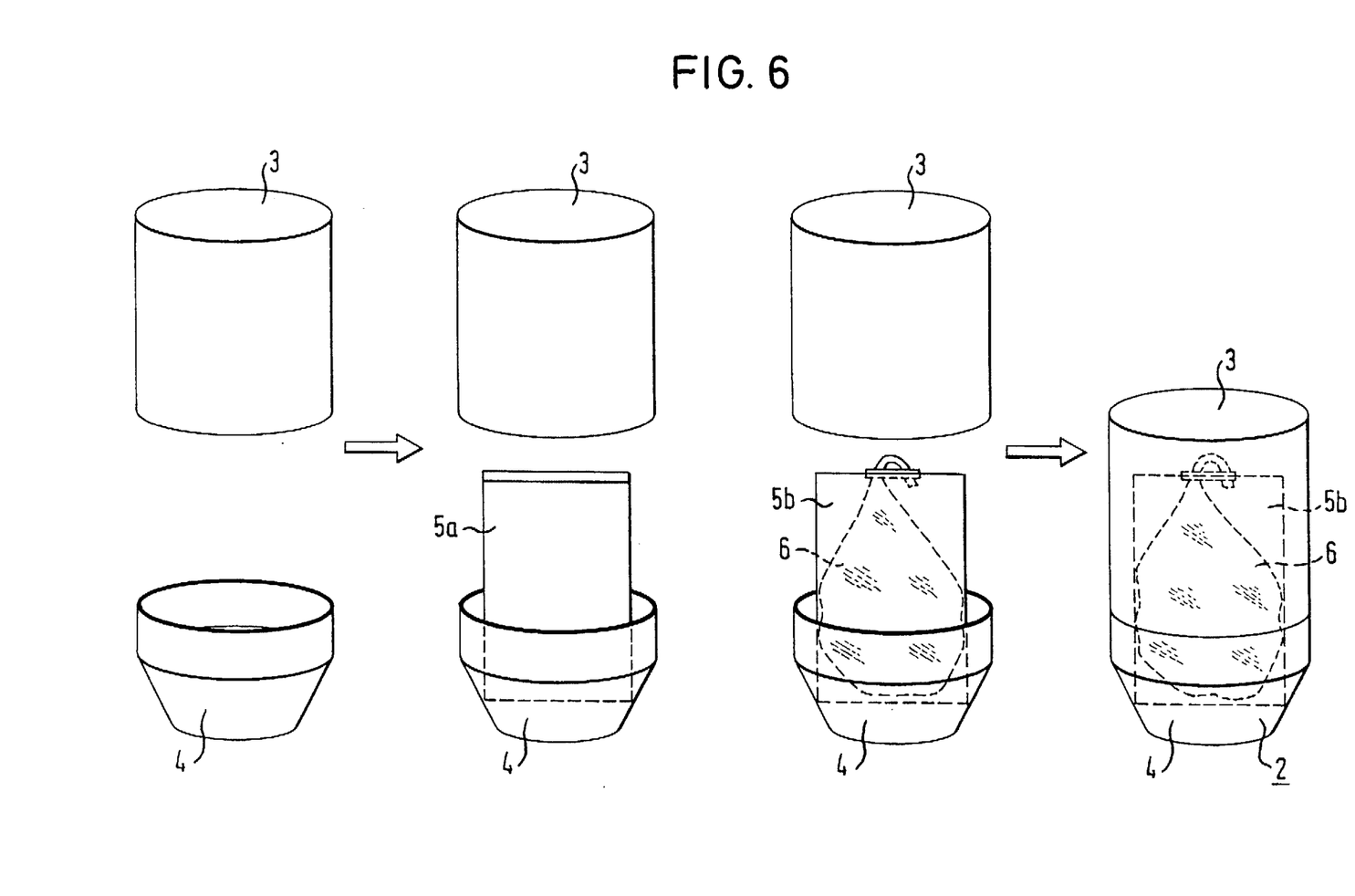
FIG. 6 shows a layout for filling a pressure vessel according to the invention with infectious waste collected in a container.

In FIG. 6, it is schematically evident how a pressure vessel 2, as previously described in relation to the preceding Figures, is filled with infectious waste. It is schematically shown in the far left-hand representation how the pressure vessel consisting of an upper part 3 and a lower part 4 is opened. As already explained above, a folding mechanism can be formed between parts 3 and 4 in the practical embodiment, or a sliding mechanism could also be designed in which upper part 3, corresponding to the sketch in FIG. 6, is pushed upwards away from lower part 4. The two center drawings in FIG. 6 show an alternative whereby a sealed plastic container 5a and a sealed plastic waste bag 6 are used for filling. In one instance, the infectious waste to be treated is collected in a stable plastic container 5a, sealed with a lid, then conveyed in a sealed state to the disinfection installation and thus introduced into the pressure vessel. In the other instance, the infectious waste is collected in a plastic bag 6 which is then sealed and conveyed in this manner to the disinfection installation. As shown in FIG. 6, the plastic bag 6 can then be placed in an open plastic container 5b which is introduced into pressure vessel 2. Once they have been introduced into pressure vessel 2, both the plastic container 5a sealed with a lid and the sealed plastic bag 6 remain sealed. As shown on the far right of FIG. 6, the pressure vessel 2 loaded with infectious waste is finally pressure-sealed by folding or pushing together the two pressure-vessel parts 3 and 4.

As will also be explained in the description of the associated disinfection method, the plastic containers 5a filled with infectious waste, and the plastic bags 6 each have a coating that absorbs infrared light.

The disinfection method according to the invention, as can be performed using the previously described installation, will now be explained by way of the following examples.

Pressure vessels 2, as previously described, are first filled with infectious waste which is located either in sealed plastic containers 5a or sealed plastic bags 6. Once the individual pressure vessels 2 have been filled, they are pressure-sealed and the disinfection program is started.

Pressure vessels 2 are first evacuated by means of vacuum pump 11, whereby the exhaust air is passed via bacterial filters 23, 24 and charcoal filter 25. During evacuation, the pressure vessel interior is momentarily exposed to infrared light by infrared radiation sources 27. This causes the plastic lid provided with the previously mentioned coating that absorbs infrared light to heat up so that the plastic melts in the vicinity of the coating, and an opening in the container or bag is produced. The opening of the reference rupture point in the form of melting out is assisted by the overpressure inside the vessel or bag in proportion to the pressure vessel interior being evacuated. On account of this opening formed in plastic container 5a or plastic bag 6, the air or gases are, during further evacuation, removed both from the pressure vessel itself and from the inside of the container or of the bag.

Once a lower operating pressure of app. 40 mb has been reached, pressure vessel 2 is shut off in a pressure-sealed manner by air shutoff valve 18 and then heated water from water tank 14 is fed by boiler or flow heater 16 via water line 20 and water inlet valve 17 into the pressure vessel. The injected quantity of water is chosen somewhat higher than would be necessary for completely filling the pressure vessel with saturated water vapor. The injected water evaporates as a result of the low atmospheric pressure. The water vapor should be heated to at least 105° C. for the purpose of disinfection.

Air shutoff valve 18 is now opened and the heated water vapor expands in airing and ventilation line 22 as far as shutoff valves 30 and 31 which are arranged ahead of bacterial filter 23 or overpressure vessel 15. This ensures that airing and ventilation line 22, through which the evacuated air had previously been passed from the pressure vessel and the container filled with infectious waste, is also disinfected. Otherwise, when subsequently airing or venting the pressure vessel, any bacteria or germs present in the evacuation gases would be reintroduced into the pressure vessel after disinfection treatment.

A dwell time of app. 3 minutes then begins in order to ensure that the material filling up the pressure vessel is evenly heated up. This is followed by a disinfection time of app. 5 minutes during which the filling material to be disinfected and the aerating/ventilating lines are disinfected.

After the disinfection period has elapsed, the pressure vessel is aired or vented in any known manner, for example, by opening the valve 30 while the vacuum pump 11 is off or by otherwise connecting the line 22 to atmosphere. The pressure vessel can then be opened so as to remove the disinfected waste.

Should an object, which bursts during treatment and generates an overpressure in the pressure vessel, be found in the infectious waste to be treated, relief valve 19 responds, and the gas affected by overpressure is diverted to overpressure vessel 15.

Pressure vessels 2 are dimensioned in the exemplary embodiment such that they can hold plastic containers or plastic bags which each have at least one reference rupture point which can be melted open by infrared light and which have a volume of up to 60 liters. As is evident from the—albeit only schematic—representation in FIG. 1, the dimensions of the pressure vessels are chosen to be only insignificantly larger than those of the plastic containers to be held. Temperature sensors and pressure transducers are also located in the pressure vessel itself so as to control and monitor the disinfection process.

Since in the above described method, the plastic containers are only loaded thermally and not mechanically, they can be re-used after appropriate cleaning if the reference rupture point, which is triggered thermally, is arranged for example in the container lid so that only the lid need be replaced. Because the plastic containers can be re-used, the result is also a cost-effective operation when disinfecting infectious waste. Material can also be economized by using thinner wall thicknesses for the plastic containers, as they themselves are not mechanically stressed as a result of over or underpressure.

A substantial advantage in the method according to the invention is obtained by the time saved for a complete disinfection process. Since the heated water already evaporates at 40 mb, the energy for the evaporation heat no longer has to be additionally expended, which saves time and energy. Whereas in conventional methods, a complete treatment cycle usually lasts between one and several hours, just some 20 minutes are required for the above described disinfection cycle.

Infectious waste can therefore be treated cost-effectively, rapidly and in varying quantities thanks to the method according to the invention and the invention's apparatus for producing this method.

We claim:

1. In a method for disinfecting or sterilizing infectious waste, comprising the steps of:

introducing said infectious waste into a pressure chamber;

evacuating said pressure chamber;

feeding a heated fluid, the quantity of which is at least sufficient to fill the pressure chamber's volume with saturated steam and the temperature of which corresponds to the desired disinfection or sterilization temperature, into said pressure chamber;

allowing said heated saturated steam, which fills said pressure chamber, to remain for a dwell time provided for the purpose of disinfection or sterilization;

airing said pressure chamber and removing said disinfected or sterilized waste, the improvement comprising placing said infectious waste in a sealed container having a reference rupture point in a wall which is melted open by infrared radiation wherein said infectious waste is introduced into said pressure chamber by placing said sealed container in said pressure chamber, and wherein during the evacuation of said pressure chamber after said infectious waste has been introduced, infrared radiation is introduced into said pressure chamber so as to open said reference rupture point which can be melted open by infrared radiation to produce a gas-permeable connection between the inside of said container and said pressure chamber.

2. A method according to claim 1, wherein at least two of said pressure chambers are alternately operated for disinfecting or sterilizing infectious waste.

3. A method for disinfecting or sterilizing infectious waste, comprising the steps of:

a) sealing the infectious waste in a container having a wall section which can be melted by infrared radiation;

b) sealing said container holding the infectious waste in a pressure chamber;

c) evacuating said pressure chamber;

d) after said pressure chamber is at least partially evacuated, exposing said container holding the infectious waste to sufficient infrared radiation to melt said wall section whereby the inside of said pressure chamber is open to the infectious waste in said container; and e) filling said evacuated pressure chamber with a sufficient quantity of steam at a sufficiently high temperature and for a sufficiently long time to disinfect or sterilize the infectious waste in said pressure chamber.

4. A method for disinfecting or sterilizing infectious waste, as set forth in claim 3, and wherein the container holding the infectious waste is exposed to infrared radiation by directing the infrared radiation through an infrared transparent section of a wall of said pressure chamber.

5. A method for disinfecting or sterilizing infectious waste, as set forth in claim 3, and wherein said infrared radiation melts a thermoplastic lid coated with an infrared absorbing coating on said infectious waste container.

6. A method for disinfecting or sterilizing infectious waste, as set forth in claim 3, and further including the step of heating walls of said pressure chamber.

7. A method for disinfecting or sterilizing infectious waste, as set forth in claim 3, and wherein said evacuated pressure chamber is filled with steam by injecting water heated to at least 105° C. into said evacuated pressure chamber, said water vaporizing to form steam.

* * * * *